US012383330B2

(12) United States Patent
Bourgeault et al.

(10) Patent No.: US 12,383,330 B2
(45) Date of Patent: *Aug. 12, 2025

(54) REUSABLE MINIMALLY INVASIVE SURGICAL INSTRUMENT

(71) Applicant: Microline Surgical, Inc., Beverly, MA (US)

(72) Inventors: Mark Bourgeault, Stratham, NH (US); Shekhar Nimkar, Swampscott, MA (US); Brian Foster, Stoneham, MA (US); Christopher Alesi, Saugus, MA (US); Charity Nguyen, Lynn, MA (US); Russ Laroche, Salem, NH (US); Ishita Tyagi, Santa Clara, CA (US)

(73) Assignee: Microline Surgical, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,084

(22) Filed: Sep. 11, 2023

(65) Prior Publication Data

US 2023/0414271 A1    Dec. 28, 2023

Related U.S. Application Data

(63) Continuation of application No. 16/298,817, filed on Mar. 11, 2019, now Pat. No. 11,813,017.

(51) Int. Cl.
*A61B 18/14* (2006.01)
*A61B 10/02* (2006.01)
(Continued)

(52) U.S. Cl.
CPC ...... *A61B 18/1445* (2013.01); *A61B 10/0233* (2013.01); *A61B 2017/00407* (2013.01);
(Continued)

(58) Field of Classification Search
CPC ............ A61B 18/1445; A61B 10/0233; A61B 2017/00407; A61B 2017/00526;
(Continued)

(56) References Cited

U.S. PATENT DOCUMENTS 5,358,508 A * 10/1994 Cobb ..................... A61B 17/29
606/174
5,368,606 A    11/1994 Marlow et al.
(Continued)

FOREIGN PATENT DOCUMENTS

CN    103298419 A1    9/2013
EP    2522285 A1    11/2012
(Continued)

OTHER PUBLICATIONS

"Hand Instruments—The HiQ+ Series", Olympus Winter & IBR GMBH, Dec. 17, 2018, 24 pages.
(Continued)

*Primary Examiner* — Michael F Peffley
*Assistant Examiner* — Bo Ouyang
(74) *Attorney, Agent, or Firm* — Kilpatrick Townsend & Stockton LLP

(57) ABSTRACT

A reusable tip for minimally invasive surgical instruments can include an end effector, a two-part hub, and a yoke. The end effector can include one or more movable portions enabling the end effector to move between first (e.g., open) and second (e.g., closed) positions via manipulation of the yoke within the hub. The hub can include a proximal hub and a distal hub coupled together. The end effector can be coupled to the distal hub, which can be made of a metal to provide high strength and secure shape to the distal hub. The proximal hub can be made of an autoclavable insulation (Continued)

material capable of maintaining a removable coupling with a control shaft. The proximal hub can be made of polyetheretherketone (PEEK).

20 Claims, 7 Drawing Sheets

(51) Int. Cl.
*A61B 17/00* (2006.01)
*A61B 18/00* (2006.01)
(52) U.S. Cl.
CPC .............. *A61B 2017/00526* (2013.01); *A61B 2018/00077* (2013.01); *A61B 2018/00595* (2013.01); *A61B 2018/00982* (2013.01); *A61B 2018/146* (2013.01)
(58) Field of Classification Search
CPC .......... A61B 2018/00077; A61B 2018/00595; A61B 2018/00982; A61B 2018/146
See application file for complete search history.

(56) References Cited

U.S. PATENT DOCUMENTS

| | | | |
|---|---|---|---|
| 5,571,137 | A | 11/1996 | Marlow et al. |
| 5,573,534 | A | 11/1996 | Stone |
| 7,776,065 | B2 | 8/2010 | Griffiths et al. |
| 7,938,839 | B2 | 5/2011 | DiFrancesco et al. |
| 7,938,842 | B1 * | 5/2011 | Chin ................. A61B 17/3201 |
| | | | 606/190 |
| 8,888,772 | B2 | 11/2014 | Aue et al. |
| 9,271,749 | B2 | 3/2016 | Kiapour et al. |
| 9,358,026 | B2 | 6/2016 | Bernhardt |
| 9,517,057 | B2 | 12/2016 | Taniguchi et al. |
| 9,872,724 | B2 | 1/2018 | Walberg et al. |
| 10,004,555 | B2 | 6/2018 | Koss |
| 10,092,350 | B2 | 10/2018 | Rothweiler et al. |
| 11,813,017 | B2 | 11/2023 | Bourgeault et al. |
| 2007/0027447 | A1 * | 2/2007 | Theroux ................ A61B 17/29 |
| | | | 606/41 |
| 2007/0088351 | A1 | 4/2007 | Ewaschuk et al. |
| 2015/0233211 | A1 | 8/2015 | Bujold et al. |
| 2015/0265340 | A1 | 9/2015 | Münnig et al. |
| 2016/0030072 | A1 | 2/2016 | Devlin et al. |
| 2016/0213415 | A1 | 7/2016 | Carter et al. |
| 2018/0160567 | A1 | 6/2018 | Williams et al. |
| 2018/0325579 | A1 * | 11/2018 | Haughton .......... A61B 18/1445 |

FOREIGN PATENT DOCUMENTS

| | | |
|---|---|---|
| JP | 6430050 A | 11/2018 |
| WO | 2011033881 A | 3/2011 |

OTHER PUBLICATIONS

"Laparoscopic Instruments—Product Catalog", AESCULAP, Dec. 17, 2018, 140 pages.
"Laparoscopy Catalog", Symmetry Surgical, Dec. 17, 2018, 54 pages.
"Marlow Nu-Tip® Laparoscopic Instruments", CooperSurgical, Dec. 17, 2018, 2 pages.
"Orange Surgical Instruments Product List Leaflet", Monopolar Reusable Handles OS-3924, OS-3925, Dec. 17, 2018, 1 page.
U.S. Appl. No. 16/298,817 , Advisory Action, Mailed On Feb. 10, 2023, 3 pages.
U.S. Appl. No. 16/298,817 , Final Office Action, Mailed On Oct. 14, 2022, 12 pages.
U.S. Appl. No. 16/298,817 , Non-Final Office Action, Mailed On Mar. 2, 2022, 11 pages.
U.S. Appl. No. 16/298,817 , "Notice of Allowability", Jun. 29, 2023, 2 pages.
U.S. Appl. No. 16/298,817 , Notice of Allowance, Mailed On May 25, 2023, 8 pages.
Application No. IN202117040992 , "First Examination Report", Apr. 11, 2023, 7 pages.
Application No. PCT/US2020/021918 , International Preliminary Report on Patentability, Mailed On Sep. 23, 2021, 9 pages.
Application No. PCT/US2020/021918 , International Search Report and Written Opinion, Mailed On Jun. 17, 2020, 15 pages.

\* cited by examiner

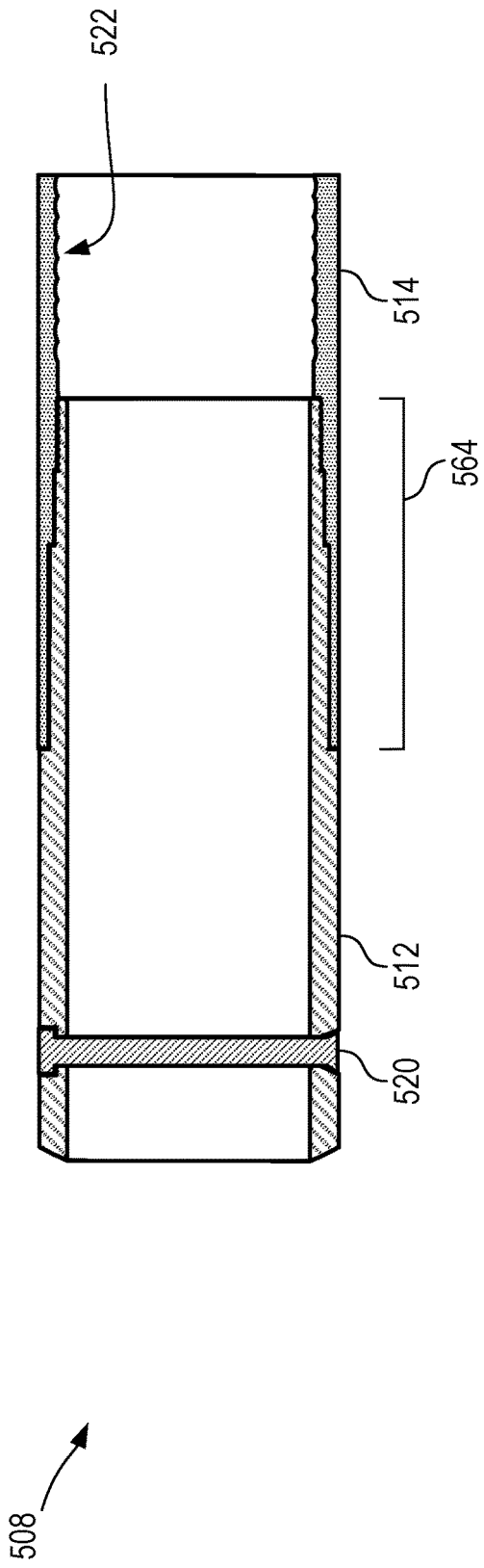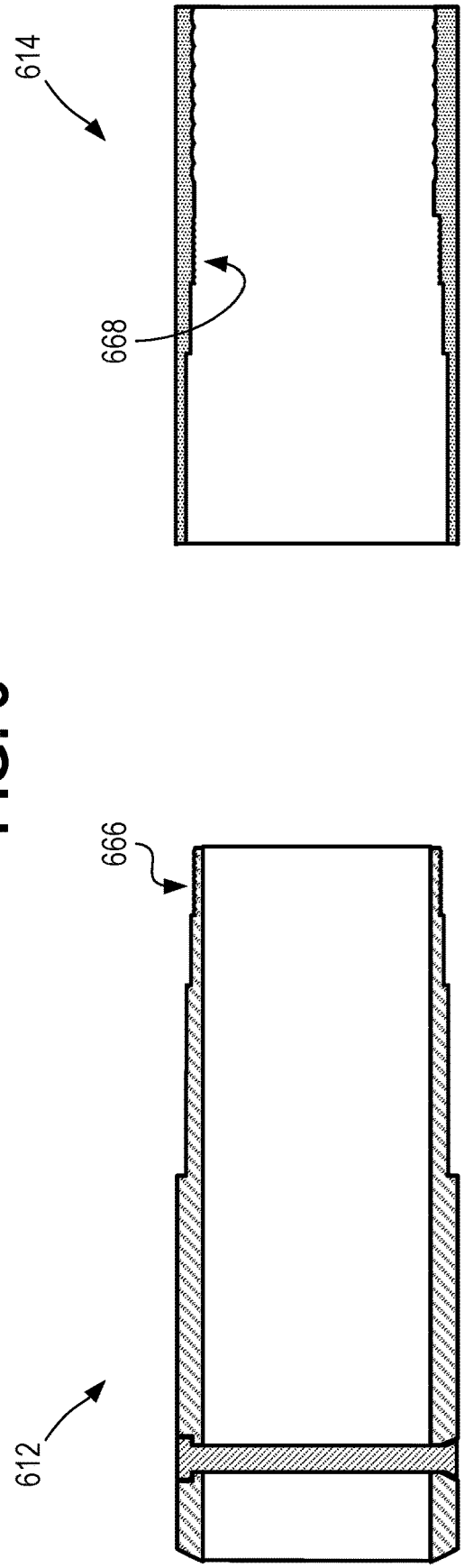
FIG. 5
FIG. 6

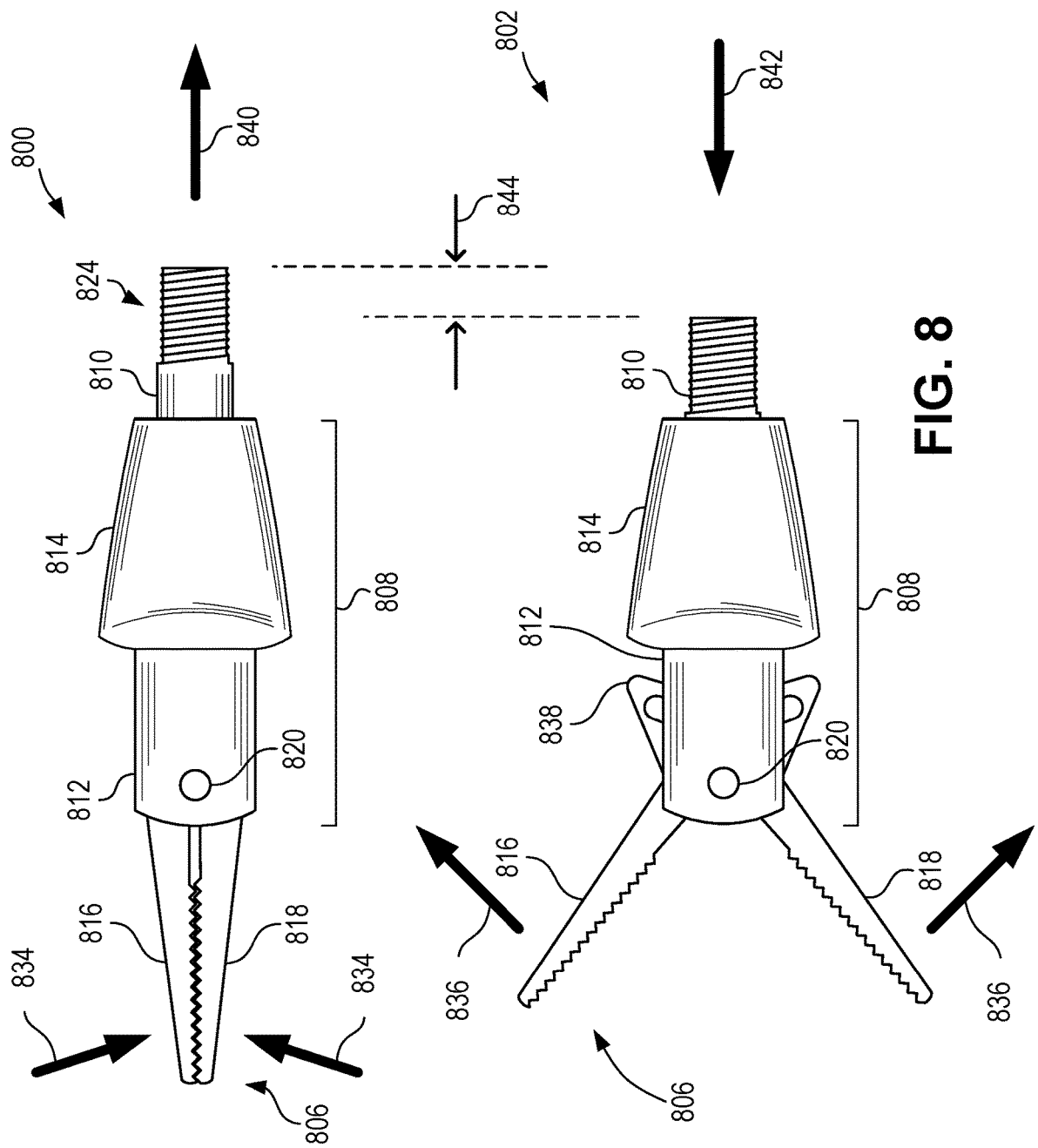

REUSABLE MINIMALLY INVASIVE SURGICAL INSTRUMENT

CROSS REFERENCE TO RELATED APPLICATIONS

This application is a continuation of U.S. application Ser. No. 16/298,817, filed Mar. 11, 2019, now U.S. Pat. No. 11,813,017, issued Nov. 14, 2023, which is hereby incorporated by reference for all purposes.

TECHNICAL FIELD

The present disclosure relates to surgical equipment generally and more specifically to reusable tips for minimally invasive surgical instruments, such as laparoscopic probes.

BACKGROUND

Minimally invasive surgical techniques can involve inserting instruments into a body cavity through existing openings or small incisions to perform surgical interventions. The surgical instruments used in such techniques are manipulated remotely, such as via robotic control or human control. For example, in endoscopic or laparoscopic surgeries, an individual may manipulate a surgical instrument within a patient using handles connected to the surgical instrument by control shafts passing into the patient. Thus, surgical interventions can be conducted with less damage to the patient, shorter healing time, and less risk of infection as compared to traditional surgery.

Often, minimally invasive surgical techniques involve the use of electrosurgical instruments. Electrosurgical instruments use the application of electrical currents to perform various surgical tasks, such as cutting, coagulation, desiccation, or fulguration of tissue. Electrical currents can pass through the control shaft and into tissue surrounding the end effector of the surgical instrument.

Many minimally invasive surgical instruments are made to be one-time use instruments. Thus, each instrument is manufactured to be a sterile instrument that, after use, is not intended to be or cannot be re-sterilized, and is discarded.

Many minimally invasive surgical instruments are designed to have a reusable handle to which different shafts can be attached. Each shaft can have a different type of end effector, such as scissors or graspers. In some cases, the entire shaft can be remoted and sterilized. However, due to the length of the shafts used in various minimally invasive surgeries, these tools can be burdensome to sterilize, such as requiring custom or extra-large sterilization pouches or occupying so much volume in an autoclave that a single set of instruments may need to be autoclaved in multiple batches. As a result, current sterilizable minimally invasive surgical instruments can take a very long time to sterilize and can require the expenditure of multiple batches worth of energy and resources.

Some single-use, disposable surgical tips have been used, comprising a one-piece hub that is partially covered by a section of polyolefin heat-shrink tubing. However, such surgical tips could not be sufficiently cleaned and sterilized for reuse. Attempts to clean and sterilize such tips resulted in loose heat-shrink tubing that carried risk of detachment during use, which could lead to inadvertent electrical conduction to adjacent tissue, loss of the tubing within a patient, and malfunction of the surgical tip due to mechanical interference from the loose tubing. As a result, surgical interventions using such tips required disposing of the tips after use, resulted in large amounts of waste and requiring institutes to maintain large inventories of new tips, thus occupying critical space and increasing costs.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include is a surgical tip comprising: an end effector movable from a first position to a second position, the end effector having a distal region for contacting tissue and a proximal region; a yoke coupled to the proximal region of the end effector for manipulating the end effector between the first position and the second position, wherein the yoke comprises a threaded proximal end, wherein the yoke and the end effector are made of an electrically conductive material, and wherein the yoke and the end effector are electrically coupled; and a hub positioned around the yoke, wherein the hub comprises a distal hub and a proximal hub, wherein the end effector is coupled to the distal hub at a pivot, wherein the proximal hub is made of a non-conductive material, and wherein the proximal hub comprises a proximal threaded end.

In some cases, the proximal hub is made of Polyetheretherketone. In some cases, the proximal hub is coupled to the distal hub by a threaded connection. In some cases, the proximal hub is coupled to the distal hub with an epoxy. In some cases, the threaded proximal end of the yoke and the threaded proximal end of the proximal hub are coaxially threaded. In some cases, the proximal hub surrounds a portion of the distal hub. In some cases, the end effector is selected from the group consisting of scissors, graspers, a punch, and dissectors. In some cases, the distal hub includes a slot for receiving the proximal region of the end effector during movement of the end effector between the first position and the second position, and wherein the proximal hub surrounds a portion of the distal hub located proximally beyond the slot. In some cases, the proximal hub is made of material having a dielectric strength of at or greater than 130 KV/cm. In some cases, the proximal hub has an outer diameter of at or less than 6.0 mm. In some cases, the proximal hub is made of an autoclavable and sterilizable material. In some cases, the proximal hub is made of a material having a glass transition temperature at or above 120° C. In some cases, a length between a distal end of the distal hub and a proximal end of the yoke is at or less than 5 cm. In some cases, a length between a distal end of the end effector and a proximal end of the yoke is at or less than 9 cm. In some cases, the end effector comprises a stationary portion and a movable portion, wherein the stationary portion is fixed with respect to the hub. In some cases, the end effector comprises a first movable portion and a second movable portion, wherein the first movable portion and the second movable portion move with respect to the hub during movement of the end effector between the first position and the second position.

Embodiments of the present disclosure include a surgical apparatus comprising: a surgical tip as described above; and a handpiece couplable to the surgical tip, wherein the handpiece comprises an inner shaft movable axially within an outer shaft, wherein the outer shaft is couplable to the proximal hub by the proximal threaded end of the proximal hub, and wherein the inner shaft is couplable to the yoke by the threaded proximal end of the yoke.

In some cases, the outer shaft is made of the same material as the proximal hub. In some cases, the outer shaft has an outer diameter that is the same size as an outer diameter of the proximal hub. In some cases, the handpiece further comprises a cautery pin electrically coupled to the inner shaft to convey electrical signals through the inner shaft and the yoke to the end effector when the surgical tip is coupled to the handpiece. In some cases, the surgical apparatus further comprises an additional surgical tip, wherein the handpiece is couplable to the additional surgical tip after decoupling of the surgical tip from the handpiece, wherein the additional surgical tip comprises an additional end effector that is different from the end effector of the surgical tip.

Embodiments of the present disclosure include a method, comprising: providing a surgical tip as described above; coupling the surgical tip to a handpiece, wherein the handpiece comprises an inner shaft movable axially within an outer shaft, and wherein coupling the surgical tip to the handpiece comprises coupling the outer shaft of the handpiece to the proximal hub of the surgical tip by the proximal threaded end of the proximal hub, and coupling the inner shaft of the handpiece to the yoke of the surgical tip by the threaded proximal end of the yoke; decoupling the surgical tip from the handpiece; and autoclaving the surgical tip.

In some cases, the method further comprises coupling the autoclaved surgical tip to the handpiece or an additional handpiece; and contacting tissue with the end effector of the surgical tip during a surgical procedure. In some cases, the method further comprises applying electrical current to tissue through the yoke and the end effector. In some cases, the electrical current conveyed through the yoke is not conveyed through the proximal hub.

BRIEF DESCRIPTION OF THE DRAWINGS

The specification makes reference to the following appended figures, in which use of like reference numerals in different figures is intended to illustrate like or analogous components.

FIG. 5 is a cross-sectional top view depicting a hub of a surgical instrument tip with the proximal hub and distal hub coupled together according to certain aspects of the present disclosure.

FIG. 6 is a cross-sectional top view depicting a hub of a surgical instrument tip with the proximal hub and distal hub separate according to certain aspects of the present disclosure.

FIG. 8 is a set of schematic side views depicting surgical instrument tips with flared proximal hubs in closed and open positions according to certain aspects of the present disclosure.

DETAILED DESCRIPTION

Figure 1:
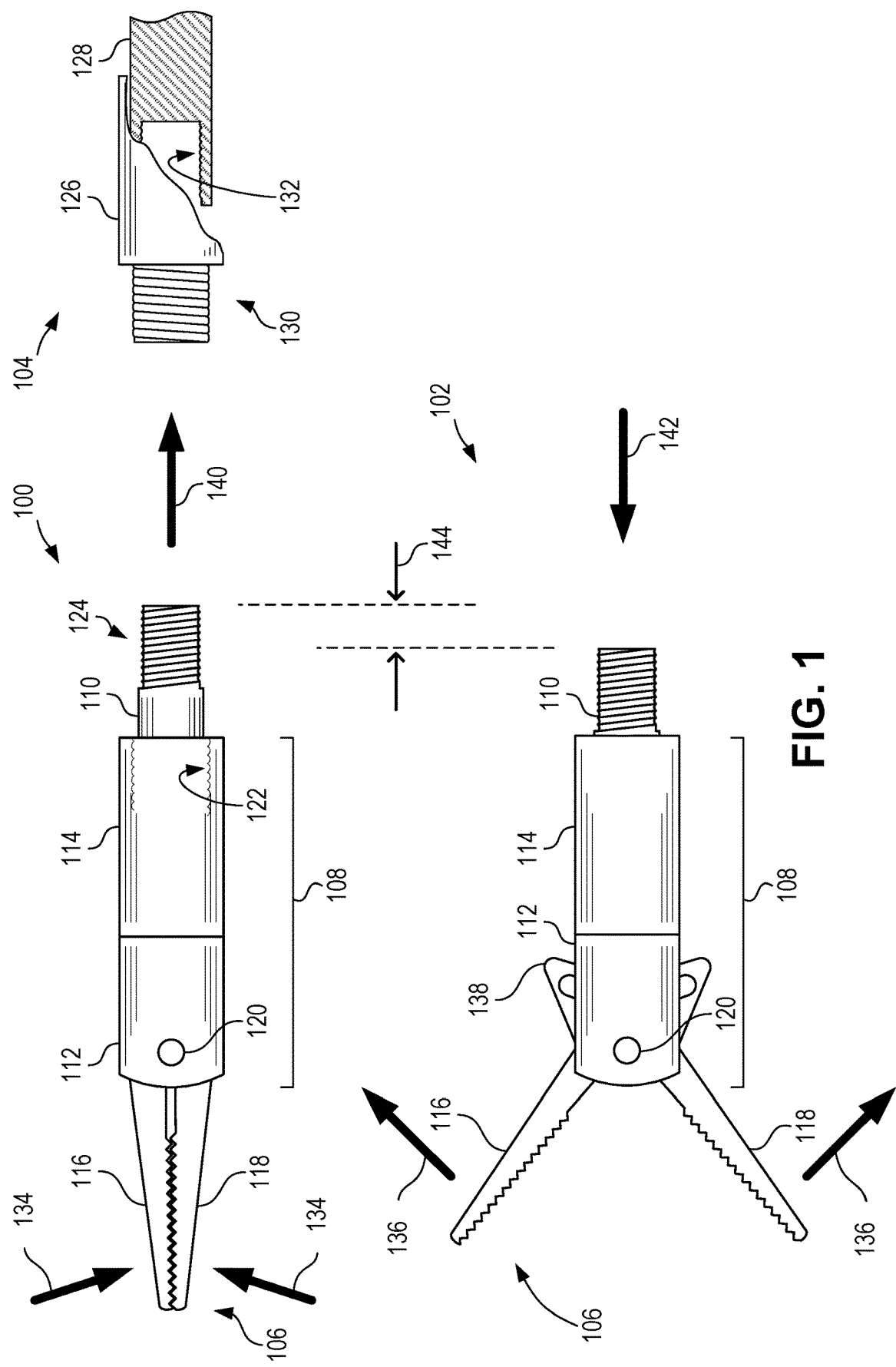
FIG. 1 is a set of schematic side views depicting surgical instrument tips in closed and open positions and a partial-cutaway schematic side view of a distal portion of a control shaft according to certain aspects of the present disclosure.

Certain aspects and features of the present disclosure relate to reusable tips for minimally invasive surgical instruments. The reusable tip can include an end effector, a hub, and a yoke. The end effector can include one or more movable portions enabling the end effector to move between a first (e.g., open) position and a second (e.g., closed) position via manipulation (e.g., axial manipulation) of the yoke within the hub. The hub can include a proximal hub and a distal hub that are coupled together, such as via a threaded coupling and/or epoxy. The end effector can be coupled to the distal hub, which can be made of a metal to provide high strength and secure shape to the distal hub. The proximal hub can be made of an autoclavable insulation material capable of maintaining a removable coupling with a control shaft. The proximal hub can be made of polyetheretherketone (PEEK).

Certain aspects of the present disclosure relate to reusable tips for minimally invasive surgical instruments. These surgical tips can be configured for any suitable type of surgery, such as robot-conducted or robot-assisted surgeries, endoscopic surgeries, laparoscopic surgeries, or any other suitable minimally invasive surgery. In some cases, certain aspects of the present disclosure can be especially beneficial for laparoscopic surgical instruments due to the style of surgical instruments used in laparoscopic surgeries.

A minimally invasive surgical instrument can include a surgical tip removably attachable to a handle via a control shaft. The handle can be non-removably coupled to the control shaft, although that need not always be the case. The combination of a handle and a control shaft, whether the control shaft is removable or not, can be known as a handpiece. The surgical tip is removably couplable to the control shaft, permitting the surgical tip to be cleaned and sanitized on its own. Further, the functionality of the surgical instrument can be quickly changed on the fly, such as mid-surgery, by removing one surgical tip and attaching a different surgical tip. In this fashion, a single handle and control shaft can be used with multiple surgical tips during a surgical procedure, resulting in only a single handle and control shaft set needing to be cleaned and sterilized despite the use of multiple different surgical tips with that same handle and control shaft. As used herein, the surgical instrument can be referred to as having the handle at its proximal end and the surgical tip at its distal end. Thus, the terms distal and proximal as used herein can refer to directions away from and towards the handle-end of the surgical instrument.

The handle can include one or more grips for actuating the end effector of the surgical tip. The handle can be configured in different fashions depending on the desired functionality. Some handles can have ratcheting action (e.g., ratcheting grips) while others do not. In some cases, handles can include one or more electrical posts (e.g., cautery posts) to convey electrical current to the control shaft. Some handles can have short electrical posts while others have long electrical posts. In some cases, a handle can include a flush port to facilitate cleaning of the handle and/or attached control shaft. In some cases, the electrical post can double as a flush port. In some cases, a rotation knob can control rotation of the control shaft, which can in turn control rotation of the end effector of the surgical tip.

In some cases, the control shaft can be permanently attached to the handle, although that need not always be the case. The control shaft can be made of an outer shaft and an inner shaft. The outer shaft can be made of an electrically insulating material, such as PEEK. The inner shaft can be moveable within the outer shaft, such as axially movable, to enable actuation of the end effector via manipulation of the inner shaft with respect to the outer shaft. The inner shaft can be made of an electrically conductive material, such as a metal. In some cases, the inner shaft can be made of the same material as the yoke, end effector, and/or distal hub of the surgical tip.

Surgical tips disclosed herein can make use of any suitable style of end effector. Suitable styles of end effectors include scissors, graspers, punches, and dissectors. As an example, suitable scissor configurations can include curved scissors, straight scissors, Metzenbaum-style scissors, hooked scissors, and the like. As an example, suitable grasper configurations can include atraumatic graspers, fenestrated graspers, clinching graspers, Babcock-style graspers, Hunter-style graspers, Allis-style graspers, and the like. As an example, suitable punches can include cupped punches, biopsy punches, and the like. As an example, suitable dissectors can include dolphin-nose-style dissectors, Maryland-style dissectors, Birkett grasper-style dissectors, and the like.

End effectors can include one or more movable portions. In some cases, an end effector can move between first and second positions by moving a single movable portion against a stationary portion, such as in a common biopsy punch. In the example of a biopsy punch, a movable portion (e.g., blade) can be forced against a stationary portion (e.g., a biopsy collection surface) to collect a biopsy. This type of action with a single movable portion can be known as single-action, and an end effector using this type of action can be known as a single-action end effector. In some cases, an end effector can have two movable portions, often opposing one another, such as in a common pair of scissors. In the example of scissors, two movable portions (e.g., scissor blades) can be moved towards one another to initiate cutting action. This type of action with two movable portions can be known as dual-action, and an end effector using this type of action can be known as a dual-action end effector. Aspects of the present disclosure can be used with single-action or dual-action end effectors. In some cases, aspects of the present disclosure can be used with no-action end effectors having no movable portions (e.g., electrosurgical electrodes).

Each surgical tip can include an end effector coupled to a hub and a yoke. The end effector can be coupled to the hub such that movement of the yoke within the hub causes the end effector to move between first and second positions. For example, the end effector can be secured to the hub by way of a rivet, with a shaft of the yoke engaging one or more slots of the end effector such that axial movement of the yoke causes one or more portions of the end effector to pivot about the rivet. In some cases, other configurations can be used. The end effector can be coupled to the hub such that it is axially fixed with respect to the hub but one or more movable portions of the end effector are rotatably movable with respect to the hub.

The yoke can be positioned within the hub, within an inner diameter of the hub. The yoke can be coupled to the end effector in any suitable fashion such that movement of the yoke with respect to the hub causes movement of the one or more movable portions of the end effector with respect to the hub. In some cases, axial movement of the yoke is translated into rotational movement of one or more movable portions of the end effector about a pivot, although this need not always be the case. In some cases, axial movement of the yoke can affect the end effector in other ways. In some cases, rotational movement of the yoke can affect the end effector. The yoke can be coupled to the one or more movable portions of the end effector, such as using a sliding linkage coupling (e.g., a pin and slot linkage). The yoke can couple to the end effector using a sliding linkage coupling or any suitable mechanical coupling for converting axial movement of the yoke into appropriate movement of the movable portion(s) of the end effector. For example, a yoke can include a shaft or pin that fits within a slot on a movable portion of an end effector such that movement of the yoke in an axial direction forces the movable portion in an upwards or downwards direction, causing the movable portion to pivot about a pivot axis. The yoke can couple to the control shaft (e.g., an inner shaft of the control shaft) through any suitable technique. In some cases, the yoke can couple to the control shaft via a threaded connection.

The hub is a multi-part hub comprising a proximal portion and a distal portion, which can be referred to as a proximal hub and a distal hub, respectively. The distal hub can be used to fixedly or movably secure portions of the end effector. For example, a single-action end effector can include a stationary portion that is fixed with respect to the distal hub and a movable portion that is movably coupled to the distal hub. In another example, a dual-action end effector can include two movable portions that are movably coupled to the distal hub. In some cases, one or more movable portions of the end effector can be movably coupled to the distal hub via rotatable coupling, such as a rivet, screw, or bolt. The distal end can serve as a fulcrum for the one or more movable portions of the end effector. In some cases, the end effector can be coupled to the distal hub to act as a class one lever (e.g., a single class one lever or a double class one lever). In some cases, the end effector can be coupled to the distal hub to act as a class three lever.

The distal hub can be made of a material having sufficient strength and/or hardness to withstand construction of the end effector (e.g., application of a rivet when a rivet is used) and repeated actuation of the end effector. In some cases, the distal hub can be made of a metal suitable for surgical tools, such as surgical stainless steel or the like. In some cases, the distal hub is made of a conductive material, although that need not always be the case. In some cases, the distal hub is made of metal to ensure repeated actuation of the end effector would not negatively impact the coupling between the end effector and the distal hub for a designed lifetime of the surgical tip. In some cases, the distal hub is made from the same material as the end effector. In some cases, the distal hub is made from the same material as the one or more movable portions of the end effector.

The proximal hub can be removably or permanently coupled to the distal hub. The proximal hub can couple the distal hub to the control shaft (e.g., to an outer shaft of the control shaft). The proximal hub can include a distal coupling portion configured to couple to the distal hub, and a proximal coupling portion configured to couple to the control shaft. The distal coupling portion can be a threaded connection, although that need not always be the case. In an example, the distal hub and proximal hub can be coupled together via a threaded connection. In some cases, the distal hub and proximal hub can be coupled together with an adhesive material, such as an epoxy. In some cases, the distal hub and proximal hub can be coupled together using multiple techniques, such as via a threaded connection and an epoxy.

In some cases, all portion(s) of an end effector that are enclosed by the distal hub can remain enclosed by the distal hub (e.g., remain within the circumference of the distal hub) throughout actuation of the end effector between first and second positions. For example, while a pair of scissors may have blades that can open further than the circumference of the distal hub, the proximal ends of the movable portions of the end effector can be configured to remain within the circumference of the distal hub during actuation. However, in some cases, actuation of the end effector between first and second positions can cause one or more proximal ends of the end effector to extend outside of the circumference of the distal hub, such as through a slot in a wall of the distal hub. In an example, certain graspers operating as class one levers may have proximal ends that extend outwards from the circumference of the distal hub through slots to permit the jaws of the grasper to fully open.

The proximal hub can act to couple the distal hub to the control shaft while also acting as an insulator. The proximal hub can be made of an insulating material (e.g., an insulator). The proximal hub can be made of a material having a sufficiently high dielectric strength. In some cases, the dielectric strength of the proximal hub can be at or greater than approximately 230 KV/cm, such as at or greater than approximately 130 KV/cm, 135 KV/cm, 140 KV/cm, 145 KV/cm, 150 KV/cm, 155 KV/cm, 160 KV/cm, 165 KV/cm, 170 KV/cm, 175 KV/cm, 180 KV/cm, 185 KV/cm, 190 KV/cm, 195 KV/cm, 200 KV/cm, 205 KV/cm, 210 KV/cm, 215 KV/cm, 220 KV/cm, 225 KV/cm, 230 KV/cm, 235 KV/cm, 240 KV/cm, 245 KV/cm, and/or 250 KV/cm.

Generally, the surgical tip is made of metal parts except for the proximal hub. For example, the yoke, end effector, and distal hub can be made of a metal, which can be the same type of metal. Since these metal parts are generally electrically conductive, the proximal hub can be made from an electrically insulating material to protect non-targeted tissue surrounding the surgical tip during use. The proximal hub can act to insulate the yoke and at least a portion of the distal hub from surrounding tissue, such as during a surgical procedure. Since the yoke can convey electrical signals to the end effector in some surgical procedures, protection to surrounding tissue can be important to reduce the risk of inadvertent damage to non-targeted tissue. Non-targeted tissue can include any tissue surrounding the surgical tip during use to which electrical current is not desired to be directed, such as tissue not in contact with the end effector. The proximal hub can surround a portion of the distal hub. In some cases, the proximal hub can surround at least 10%, 15%, 20%, 25%, 30%, 35%, 40%, 45%, 50%, 55%, 60%, 65%, 70%, 75%, 80%, 85%, 90%, 95%, and/or 100% of the length of the distal hub. In some cases, this portion of the distal hub that is surrounded can be measured from a proximal end of the distal hub. In cases where the distal hub comprises a slot or other opening, such as to pass one or more proximal ends of an end effector through during actuation of the end effector, the proximal hub can extend from the proximal end of the distal hub up to or approximately up to the slot or other opening. In some cases, such as if proximal end(s) of the end effector remain entirely within the distal hub during actuation of the end effector, the proximal hub can extend up to or approximately up to the distal end of the distal hub.

In some cases, the proximal hub is made from a thermoplastic polymer that is suitable for use in surgical tools and is sterilizable. In some cases, the proximal hub is made from PEEK. In some cases, the use of PEEK can enable the proximal hub to resist damage from inadvertent contact with other tools and surfaces. In some cases, a PEEK proximal hub can resist damage better than a heat-shrink insulator surrounding a single-piece hub. The proximal hub can be made from a material having a glass transition temperature that is at or above 121° C. or 132° C. (e.g., at or above 140° C., or 143° C.). In some cases, the proximal hub can be made from a material having a melting temperature that is at or greater than 300° C. (e.g., at or above 340° C. or 343° C.). The sufficiently high glass transition temperature and/or melting temperature can ensure the proximal hub does not lose shape or integrity when subjected to sterilization procedures in an autoclave, which can reach temperatures of up to 121° C. (e.g., for gravity-based sterilizers) or 135° C. (e.g., for vacuum-based sterilizers). In some cases, the proximal hub can be made of a material having a glass transition temperature above a maximum temperature of a sterilization procedure for sterilizing the surgical tip. Such a sterilization procedure can be a sterilization procedure shared with other equipment commonly used with the surgical tip, such as a scalpel used to create an incision into which the surgical tip can be maneuvered.

The proximal hub can be coupled to the control shaft through any suitable technique. In some cases, the proximal hub is coupled to the control shaft via a threaded connection. To ensure a reliable connection between the proximal hub and the control shaft, the proximal hub can be made of a material capable of retaining any coupling features used to couple the proximal hub to the control shaft, such as threads. In some cases, the proximal hub can contain threads on an inner diameter of the proximal hub, which engage threads on an outer diameter of a portion of the outer shaft of the control shaft, however this need not always be the case. In some cases, the threaded connection between the proximal hub and the control shaft and the threaded connection between the yoke and the control shaft are coaxial.

The entire surgical tip can be of any suitable dimensions. In some cases, a surgical tip for minimally invasive surgeries can be at or less than 9 cm in length from the distal end of the end effector to the proximal end of the yoke. In some cases, the surgical tip can be at or less than 9, 8.5, 8, 7.5, 7, 6.5, or 6 cm from the distal end of the end effector to the proximal end of the yoke. In some cases, a surgical tip for minimally invasive surgeries can be at or less than 5 cm in length from the distal end of the distal hub to the proximal end of the yoke. In some cases, the surgical tip can be at or less than 6.5, 6, 5.5, 5, 4.5, 4, 3.5, or 3 mm from the distal end of the distal hub to the proximal end of the yoke. In some cases, the surgical tip can have a length that is at or less than approximately 40%, 38%, 36%, 34%, 32%, 30%, 28%, 26%, 24%, 22%, 20%, 18%, 16%, 14%, 12%, 10%, 8%, 6%, and/or 4% of the length of a control shaft coupled to the surgical tip. In some cases, the surgical tip can have a diameter that is at or less than 15, 14, 13, 12, 11, 10, 9, 8, 7, 6, or 5 mm in diameter. In some cases, the hub can have an outer diameter that is at or less than 12, 11, 10, 9, 8, 7, 6, or 5 mm in diameter.

In some cases, the proximal hub can have an outer diameter that is the same as an outer diameter of the control shaft (e.g., outer diameter of an outer shaft of the control shaft). In some cases, the proximal hub can have an outer diameter that is constant throughout its length. However, in some cases, the outer diameter of the proximal hub can become larger and optionally also smaller extending distally from a proximal end of the proximal hub. In some cases, a proximal hub with a flared diameter can provide a contiguous outer surface at the coupling between the proximal hub and the control shaft, while also providing a thicker proximal hub over portions of the distal hub, such as to provide a stronger insulating effect.

The entire surgical tip disclosed herein can be cleanable and sterilizable. In some cases, the entire surgical tip can be sterilizable through the use of an autoclave (e.g., autoclavable). The materials and construction of the components of the surgical tip can be suitable for standard operating room cleaning and sterilizing procedures.

The ability to remove the relatively small surgical tip from the control shaft and handle permit the relatively small surgical tip to be easily handled during any initial cleaning steps, and thereafter easily sterilized in bulk with other equipment. A single surgical tip as disclosed herein can fit within relatively small sterilization pouches, permitting numerous surgical tips to be sterilized at once. By contrast, sterilizable laparoscopic equipment comprising a tip and non-removable control shaft (e.g., larger than 9 or 10 cm in overall length) may require the use of large and/or customized sterilization pouches, and may occupy so much room in an autoclave that one or only a few items can be sterilized at a time.

Further, the relatively small size of the surgical tip disclosed herein can permit multiple different styles of surgical tip to be stored in a relatively small volume, at least as compared to sterilizable laparoscopic equipment comprising a tip and non-removable control shafts. For example, numerous surgical tips as disclosed herein can be stored in a volume (e.g., in a container) without needing to store a control shaft for each tip. Rather, a single handle and control shaft can be stored, to which any desired surgical tip can be attached.

Additionally, due to the modular nature of certain aspects of the disclosure, any number of tips can be combined with any number of handles and/or control shafts to achieve the desired surgical instrument for a particular surgery. For example, different handle options can include handles with or without ratcheting grips, with different sized electrical posts, and with different style rotation knobs. Further, different control shaft options can include different length control shafts (e.g., 25 cm, 34 cm, 42 cm, or other lengths). Thus, to provide a wide array of surgical instruments, aspects of the present disclosure can provide a set of surgical tips and a set of handles and/or control shafts which can be mixed and matched as necessary to achieve the desired instrument. By contrast, standard laparoscopic tools with surgical tips non-removably attached to control shafts require a new tip for each and every potential instrument length for each and every potential type of instrument, thus requiring the storage of many more items that occupy larger volumes of space than the surgical tips according to certain aspects of the present disclosure.

Aspects and features of the present disclosure enable minimally invasive surgical equipment that is easy and efficient to store, is easy to use, has well-insulated surgical tips, can be easily and efficiently sterilized, and is highly customizable.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a set of schematic side views depicting surgical instrument tips 100, 102, in closed and open positions and a partial-cutaway schematic side view of a distal portion of a control shaft 104 according to certain aspects of the present disclosure. Surgical tip 100 can comprise an end effector 106, a multi-part hub 108, and a yoke 110. The yoke 110 is positioned within hub 108 and axially movable with respect to the hub 108 to actuate the end effector 106. Surgical tip 100 can have an end effector 106 in a first (e.g., closed) position. Surgical tip 102 can be surgical tip 100 with the end effector 106 in a second (e.g., open) position.

The end effector 106 can include one or more movable portions. As depicted in FIG. 1, the end effector 106 includes a first movable portion 116 and a second movable portion 118. The first and second movable portions 116, 118 are rotatable about a pivot 120 secured to hub 108. The pivot 120 can be secured to the distal hub 112 of the multi-part hub 108. Thus, the end effector 106 can be coupled to the distal hub 112 of the multi-part hub 108. The first and second movable portions 116, 118 can be movable coupled with respect to the yoke 110 to permit the first and second movable portions 116, 118 to move between a first position as depicted with respect to surgical tip 100 and a second position as depicted with respect to surgical tip 102 when the yoke 110 is moved axially with respect to the hub 108. For example, movement of the yoke 110 in direction 140 can cause the first and second movable portions 116, 118 to move in inward directions 134 to close the first and second movable portions 116, 118 against one another, while movement of the yoke 110 in direction 142 can cause the first and second movable portions 116, 118 to move in outward directions 136 to open and separate the first and second movable portions 116, 118 from one another. Movement of the yoke 110 over distance 144 can represent actuation of the end effector 106 between a first position and a second position. As depicted in FIG. 1, the first and second movable portions 116, 118 are jaws of a grasper, although other movable portions can be used.

In some cases, a movable portion of an end effector 106 can have a proximal end that sticks out beyond a circumference of the distal hub 112 when in the first or second position. As depicted in FIG. 1, the first and second movable portions 116, 118 of surgical tip 102 have proximal ends 138 that move along a path during actuation of the end effector 106, which path takes the proximal ends 138 outside of the circumference of the distal hub 112. The distal hub 112 can include one or more slots through which the proximal ends 138 may pass. The proximal hub 114 can overlap a portion of the distal hub 112 up to or approximately up to such slot(s). In some cases, such as if no slot exists because the proximal ends of the end effector remain within the circumference of the distal hub during actuation, the proximal hub can overlap a portion of the distal hub that extends for up to or approximately up to the pivot 120 or up to or approximately up to the distal end of the distal hub.

The multi-part hub 108 can comprise a distal hub 112 coupled to a proximal hub 114. While the distal hub 112 can be made of a metal, such as the same metal used for the end effector 106 and/or the yoke 110, the proximal hub 114 can be made of an insulator, such as PEEK. The proximal hub 114 can overlap and surround a portion of the distal hub 112, although that need not always be the case.

The surgical tip 100 can removably couple to a control shaft 104. The control shaft 104 can include an inner shaft 128 and an outer shaft 126. For illustrative purposes, the outer shaft 126 is depicted in a partial-cutaway view and the inner shaft 128 is shown in a cutaway side view.

The inner shaft 128 can be axially movable within the outer shaft 126 to facilitate actuation of the end effector 106 via axially moving the yoke 110. The inner shaft 128, as well as the yoke 110 and end effector 106, can be made of electrically conductive materials, such as electrically conductive metal. The outer shaft 126 can be made of an electrically insulating material, such as PEEK. The outer shaft 126 can be made of the same material as the proximal hub 114.

The proximal hub 114 can removably couple to the outer shaft 126 of the control shaft 104 and the yoke 110 can removably couple to the inner shaft 128 of the control shaft 104. The proximal hub 114 can include threads 122 (e.g., internal threads) that engage threads 130 (e.g., external threads) of the outer shaft 126. The yoke 110 can include threads 124 (e.g., external threads) that engage threads 132 (e.g., internal threads) of the inner shaft 128. For illustrative purposes, threads 122 are depicted in dotted line for surgical tip 100. In some cases, threads 122, 124 are coaxial. Likewise, threads 130, 132 can be coaxial.

As used herein with regards to FIG. 1 and other suitable figures, movement of an inner shaft 128 or movement of a yoke 110 refers to movement of the inner shaft 128 or yoke 110 with respect to the outer shaft 126 or hub 108, respectively. Because the hub 108 is axially fixed with respect to the outer shaft 126 via a coupling (e.g., threaded coupling) between the outer shaft 126 and the proximal hub 114, and because the inner shaft 128 is axially fixed to the yoke 110 via a coupling (e.g., threaded coupling), movement of the inner shaft 128 axially with respect to the outer shaft 126 causes the yoke 110 to move axially with respect to hub 108, thus actuating the end effector to move between first and second positions.

Figure 2:
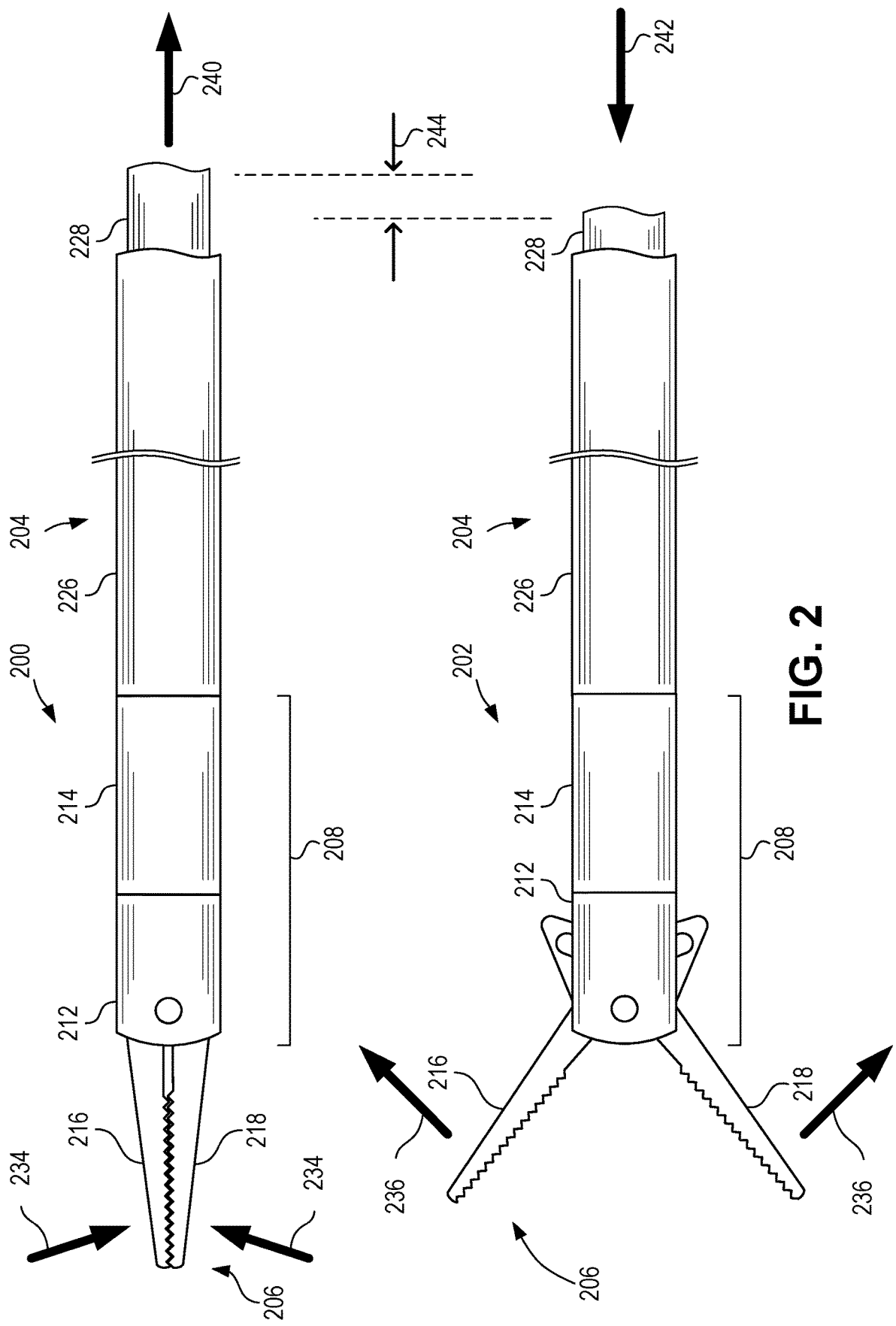
FIG. 2 is a set of schematic side views depicting surgical instrument tips coupled to control shafts in closed and open positions according to certain aspects of the present disclosure.

FIG. 2 is a set of schematic side views depicting surgical instrument tips 200, 202 coupled to control shafts 204 in closed and open positions according to certain aspects of the present disclosure. Surgical tip 200 can comprise an end effector 206, a multi-part hub 208, and a yoke. The yoke is positioned within hub 208 and axially movable with respect to the hub 208 to actuate the end effector 206. Surgical tip 200 can have an end effector 206 in a first (e.g., closed) position. Surgical tip 202 can be surgical tip 200 with the end effector 206 in a second (e.g., open) position. Surgical tip 200 and control shaft 204 can be surgical tip 100 and control shaft 104 of FIG. 1.

As depicted in FIG. 2, the surgical tip 200, 202 is coupled to the control shaft 204. The proximal hub 214 of the multi-part hub 208 is coupled (e.g., threadably coupled) to the outer shaft 226 of the control shaft 204. The yoke is coupled (e.g., threadably coupled) to the inner shaft 228 of the control shaft 204. Thus, movement of the inner shaft 228 in direction 240 can cause the first and second movable portions 216, 218 to move in inward directions 234 to close the first and second movable portions 216, 218 against one another, while movement of the yoke 210 in direction 242 can cause the first and second movable portions 216, 218 to move in outward directions 236 to open and separate the first and second movable portions 216, 218 from one another. The inner shaft 228 can move over distance 244, which can represent actuation of the end effector 206 between a first position and a second position. As depicted in FIG. 2, the first and second movable portions 216, 218 are jaws of a grasper, although other movable portions can be used.

Figure 3:
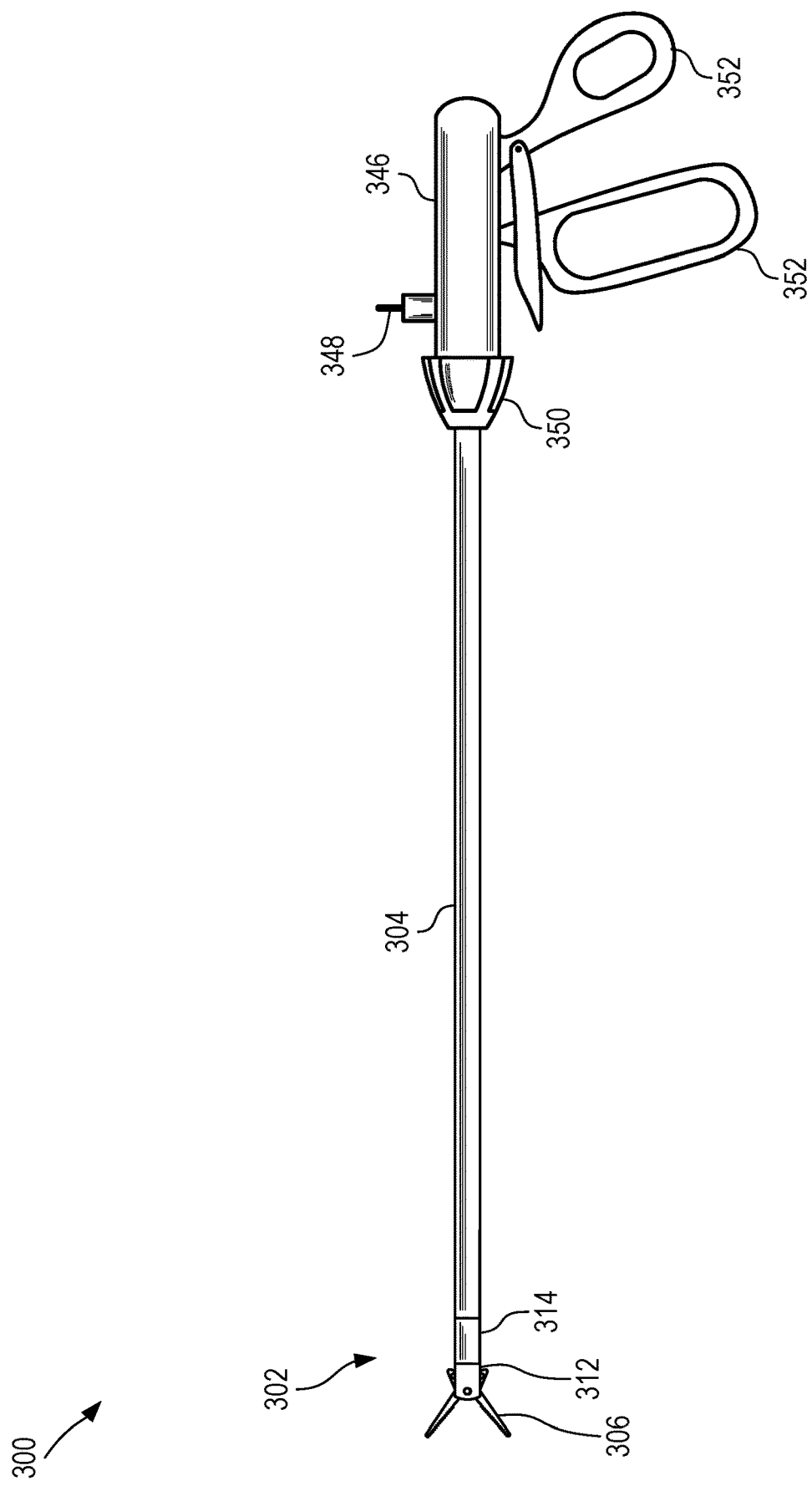
FIG. 3 is a schematic side view depicting a minimally invasive surgical instrument comprising a surgical instrument tip installed on a control shaft coupled to a handle according to certain aspects of the present disclosure.

FIG. 3 is a schematic side view depicting a minimally invasive surgical instrument 300 comprising a surgical instrument tip 302 installed on a control shaft 304 coupled to a handle 346 according to certain aspects of the present disclosure. The surgical instrument 300 can include a surgical tip 302 (e.g., surgical tip 102 of FIG. 1), a control shaft 304 (e.g., control shaft 104 of FIG. 1), and a handle 346. The surgical tip 302 is removably coupled to the control shaft 304. In some cases, the control shaft 304 can be removably coupled to the handle 346, although that need not be the case. In some cases, the control shaft 304 is permanently coupled to the handle 346.

The surgical tip 302 can include a multi-part hub comprising a distal hub 312 and a proximal hub 314. The surgical tip 302 can be removably coupled to the control shaft 304 via proximal hub 314, which is in turn permanently coupled to distal hub 312, which is movably secured to the end effector 306.

The handle 346 can include one or more grips 352 for manipulating the end effector 306 of the surgical tip 302. Movement of the one or more grips 352 (e.g., movement with respect to one another, such as towards or away from one another) can cause the inner shaft of the control shaft 304 to move axially with respect to the outer shaft, thus causing the yoke of the surgical tip 302 to move axially with respect to the hub, which in turn causes the end effector to actuate (e.g., move between first and second positions). In some cases, manipulation of the grips 352 can be further controlled by a ratcheting mechanism, although that need not always be the case. In some cases, handle 346 can include a rotary knob 350. Rotary knob 350 can be manipulated to control rotation of the control shaft 304, thus controlling rotation of the surgical tip 302.

In some cases, the handle 346 can include a port 348. Port 348 can act as one or both of an electrical port and a flush port. When used as an electrical port, port 348 can convey electrical current to the inner shaft of the control shaft 304, which can in turn convey the electrical current through to the end effector 306 of the surgical tip 302 via the yoke. This electrical current can be used for various electrosurgical techniques, including cauterizing. When used as a flush port, port 348 can permit fluid to be flushed through the control shaft 304, such as to facilitate cleaning and/or sterilization of the control shaft 304. In some cases, such as when the control shaft 304 is permanently coupled to the handle 346, the use of a flush port can be especially useful. In some cases, handle 346 can include any number of ports 348, each of which can act as one or more of an electrical port and a flush port.

Figure 4:
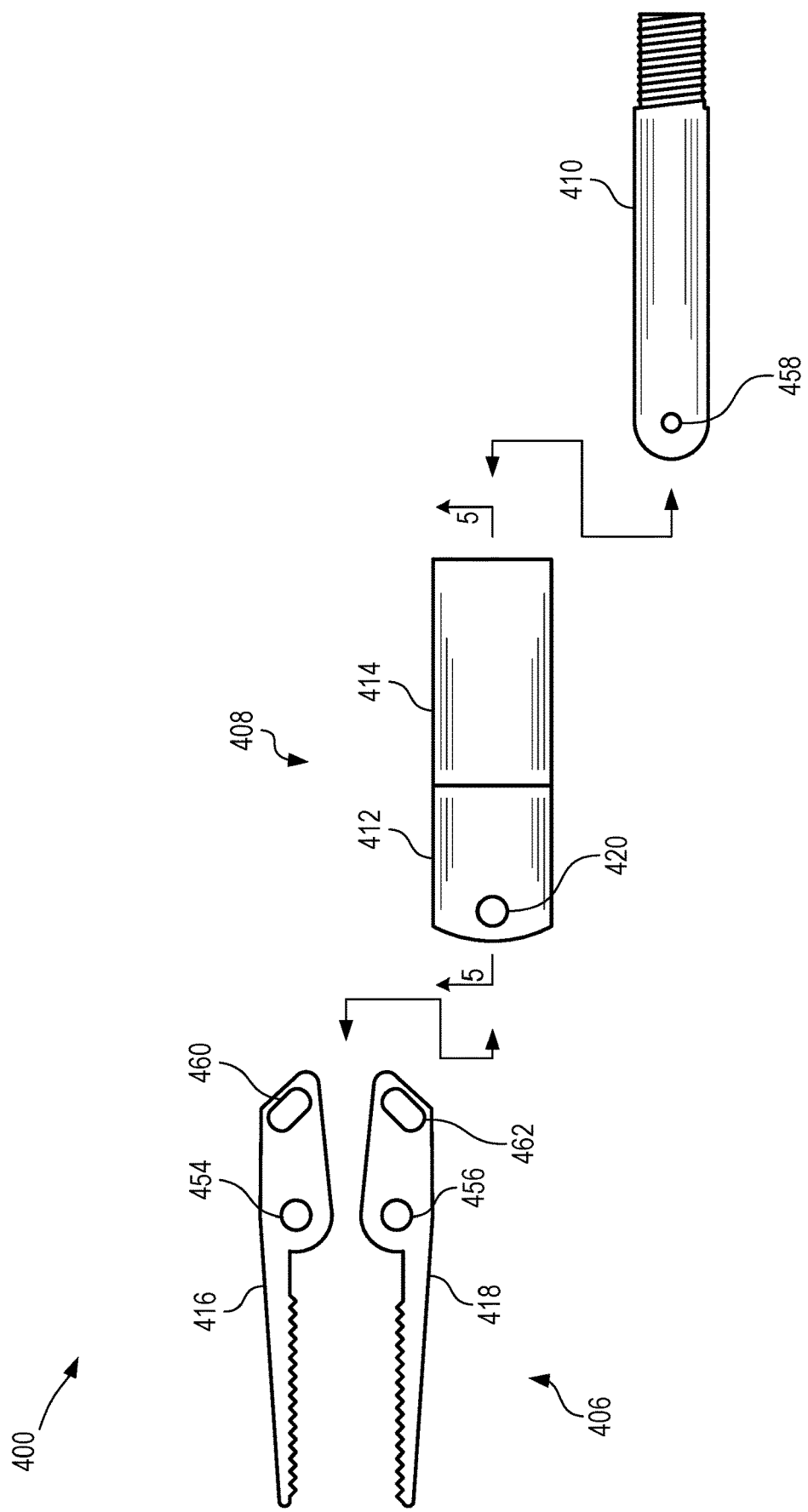
FIG. 4 is an exploded schematic side view depicting a surgical instrument tip according to certain aspects of the present disclosure.

FIG. 4 is an exploded schematic side view depicting a surgical instrument tip 400 according to certain aspects of the present disclosure. The surgical tip 400 can include an end effector 406, a multi-part hub 408, and a yoke 410. The multi-part hub 408 can be made of a distal hub 412 and a proximal hub 414 coupled together. The surgical tip 400 can be surgical tip 100 of FIG. 1.

The end effector 406 can include first and second movable portions 416, 418. First movable portion 416 can include a pivot hole 454 and a slot 460. Second movable portion 418 can include a pivot hole 456 and slot 462. When fully assembled, pivot holes 454, 456 of the end effector 406 can be aligned coaxially with one another and with pivot 420 of the distal hub 412. Pivot 420 can be a shaft-like object, such as a rivet, a screw, or a bolt, that fits within pivot holes 454, 456 to secure the end effector 406 to the distal hub 412 while leaving the first and second movable portions 416, 418 free to rotate about pivot 420.

Yoke 410 can be inserted into an inner diameter of hub 408. Yoke 410 can include a pin 458 that, when the surgical tip 400 is fully assembled, fits within both slots 460, 462 of the first and second movable portions 416, 418. As the pin 458 moves axially within the hub 408, the pin 458 will move axially with respect to the pivot 420, which is axially secured within the distal hub 412. Because of the shape of slots 460, 462, axial movement of the pin 458 will thus cause the first and second movable portions 416, 418 to move between first (e.g., open) and second (e.g., closed) positions.

FIG. 5 is a cross-sectional top view depicting a hub 508 of a surgical instrument tip with the proximal hub 514 and distal hub 512 coupled together according to certain aspects of the present disclosure. The cross-sectional viewpoint of FIG. 5 can be taken along line 5:5 of the hub 408 of FIG. 4. Hub 508 can be hub 408 of FIG. 4 or hub 108 of FIG. 1.

Distal hub 512 can be coupled to proximal hub 514 in any suitable fashion, such as using one or more of a threaded coupling and bonding (e.g., via an epoxy bond). In some cases, proximal hub 514 can be overlap a portion 564 of distal hub 512. Since distal hub 512 can be made of an electrically conductive material, the overlapped portion 564 of the proximal hub 514 over the distal hub 512 can server to insulate at least that portion 564 of the distal hub 512 from surrounding tissue, thus reducing potential for unwanted electrosurgical actions to non-targeted tissue.

Distal hub 512 can include a pivot 520, which can be any suitable object, such as a rivet. The pivot 520 can be used to secure an end effector to the distal hub 508. The proximal hub can couple to a control shaft, such as through the use of threads 522.

FIG. 6 is a cross-sectional top view depicting a hub 608 of a surgical instrument tip with the proximal hub 614 and distal hub 612 separate according to certain aspects of the present disclosure. The cross-sectional viewpoint of FIG. 5 can be taken along line 5:5 of the hub 408 of FIG. 4. Distal hub 612 can be distal hub 512 of FIG. 5, distal hub 412 of FIG. 4, or distal hub 112 of FIG. 1. Proximal hub 614 can be proximal hub 514 of FIG. 5, proximal hub 414 of FIG. 4, or proximal hub 114 of FIG. 1.

In some cases, distal hub 612 can include threads 666 capable of engaging threads 668 of proximal hub 614. The threads 668 of proximal hub 614 can be separate from or part of the threads used to couple the proximal hub 614 to a control shaft (e.g., threads 522 of FIG. 5).

In some cases, distal hub 612 and/or proximal hub 614 can include other coupling features used to facilitate coupling the distal hub 612 and the proximal hub 614 together. For example, distal hub 612 and proximal hub 614 can include roughened surfaces (e.g., cross-hatched surfaces) to which epoxy can be applied to provide a more secure bond between distal hub 612 and proximal hub 614 when they are coupled together.

In some cases, distal hub 612 and proximal hub 614 can be coupled together using threads 666, 668 and epoxy. In an example, epoxy can be applied to one or both of the distal hub 612 and proximal hub 614, such as at the threads 666, 668 or elsewhere, after which the distal hub 612 and proximal hub 614 can be screwed together. The threads 666, 668 can help keep the distal hub 612 and proximal hub 614 in place while the epoxy hardens.

Other techniques for securing the distal hub 612 to the proximal hub 614 can be used. In some cases, distal hub 612 can be removably coupled to proximal hub 614. In some cases, removable coupling between the distal hub 612 and proximal hub 614 can permit the proximal hub 614 to be replaced with a new proximal hub if it has worn out before the remainder of the surgical tip.

Figure 7:
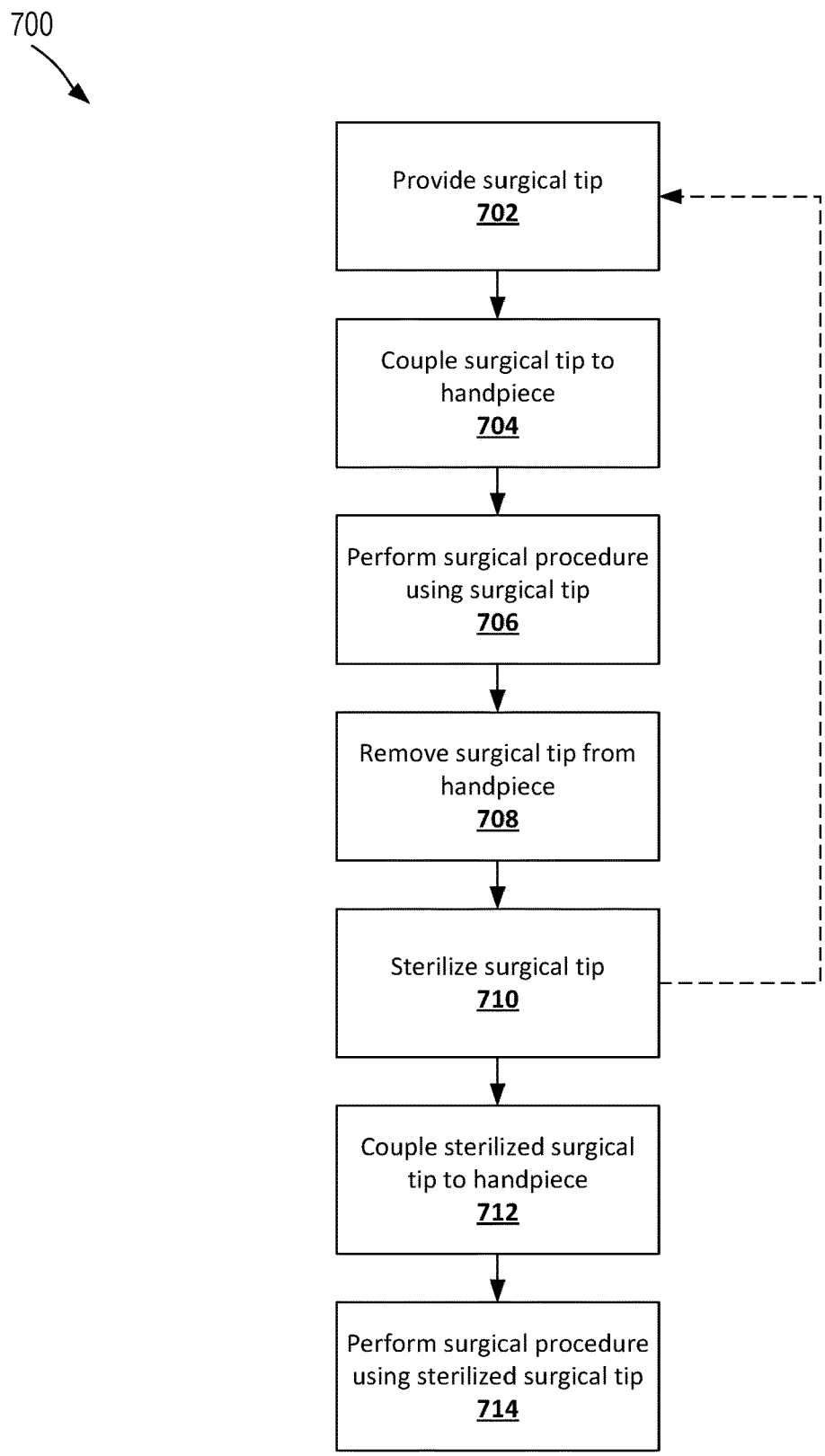
FIG. 7 is a flowchart depicting a process for using a surgical instrument tip according to certain aspects of the present disclosure.

FIG. 7 is a flowchart depicting a process 700 for using a surgical instrument tip according to certain aspects of the present disclosure. At block 702, a surgical tip can be provided. The surgical tip can be any suitable surgical tip, such as surgical tip 100 of FIG. 1. In some cases, the surgical tip can be provided from a kit of multiple surgical tips each having a different end effector. In some cases, providing a surgical tip can include providing a sterilized surgical tip in a sterilizing pouch.

At block 704, the surgical tip can be coupled to a handpiece. The handpiece can include a control shaft coupled (e.g., permanently or removably) to a handle. The surgical tip can be removably coupled to the handpiece. In some cases, coupling the surgical tip to the handpiece can include screwing a yoke of the surgical tip to an inner shaft of the handpiece. In some cases, coupling the surgical tip to the handpiece can include screwing a proximal hub of the surgical tip to an outer shaft of the handpiece. In some cases, coupling the surgical tip to the handpiece can include screwing a yoke of the surgical tip to an inner shaft of the handpiece and screwing a proximal hub of the surgical tip to an outer shaft of the handpiece.

At block 706, a surgical procedure can be performed using the surgical tip. In some cases, performing a surgical procedure can include passing an electrical current through tissue adjacent the surgical tip using the surgical tip. In some cases, passing electrical current through tissue adjacent the surgical tip can include passing electrical current through targeted tissue adjacent an end effector of the surgical tip and not applying electrical current to non-targeted tissue adjacent the proximal hub of the surgical tip. In some cases, performing a surgical procedure can include actuating an end effector of the surgical tip within a patient. In some cases, performing a surgical procedure can include actuating an end effector of the surgical tip to close one or more movable portions of the end effectors around tissue.

At block 708, the surgical tip can be removed from the handpiece. Removing the surgical tip from the handpiece can be the opposite of coupling the surgical tip to the handpiece from block 704, such as unscrewing the surgical tip from the handpiece.

At block 710, the surgical tip can be sterilized. In some cases, sterilizing the surgical tip can include cleaning and sterilizing the surgical tip. In some cases, sterilizing the surgical tip can include autoclaving the surgical tip. In some cases, sterilizing the surgical tip can include subjecting the surgical tip to temperatures at or above 121° C. or 135° C. In some cases, sterilizing the surgical tip can include placing the surgical tip in a sterilizing pouch.

At block 712, the surgical tip, after being sterilized can be coupled to a handpiece, such as the handpiece used at block 704 or another handpiece. Coupling the sterilized surgical tip to a handpiece at block 712 can occur as part of an additional surgical operation distinct from the surgical operation associated with the surgical procedure from block 706. For example, the surgical procedure from block 706 can be performed on a first patient and coupling the sterilized surgical tip to the handpiece at block 712 can be associated with (e.g., performed in preparation for) a surgical procedure to be performed on a second patient. At block 714, a surgical procedure can be performed using the sterilized surgical tip from block 712.

In some cases, instead of proceeding to blocks 712, 714, process 700 can loop from block 710 back up to block 702 for subsequent surgical procedures. In some cases, after block 708, if the surgical tip is deemed to have undergone too many use-and-sterilization cycles (e.g., blocks 702, 704, 706, 708, 710) such that the surgical tip is no longer acceptable for use, it can be disposed of or refurbished.

FIG. 8 is a set of schematic side views depicting surgical instrument tips 800, 802 with flared proximal hubs 814 in closed and open positions according to certain aspects of the present disclosure. Surgical tip 800 can comprise an end effector 806, a multi-part hub 808, and a yoke 810. The yoke 810 is positioned within hub 808 and axially movable with respect to the hub 808 to actuate the end effector 806. Surgical tip 800 can have an end effector 806 in a first (e.g., closed) position. Surgical tip 802 can be surgical tip 800 with the end effector 806 in a second (e.g., open) position. Surgical tip 800 can be surgical tip 100 of FIG. 1.

The end effector 806 can include one or more movable portions. As depicted in FIG. 8, the end effector 806 includes a first movable portion 816 and a second movable portion 818. The first and second movable portions 816, 818 are rotatable about a pivot 820 secured to hub 808. The pivot 820 can be secured to the distal hub 812 of the multi-part hub 808. Thus, the end effector 806 can be coupled to the distal hub 812 of the multi-part hub 808. The first and second movable portions 816, 818 can be movable coupled with respect to the yoke 810 to permit the first and second movable portions 816, 818 to move between a first position as depicted with respect to surgical tip 800 and a second position as depicted with respect to surgical tip 802 when the yoke 810 is moved axially with respect to the hub 808. For example, movement of the yoke 810 in direction 840 can cause the first and second movable portions 816, 818 to move in inward directions 834 to close the first and second movable portions 816, 818 against one another, while movement of the yoke 810 in direction 842 can cause the first and second movable portions 816, 818 to move in outward directions 836 to open and separate the first and second movable portions 816, 818 from one another. Movement of the yoke 810 over distance 844 can represent actuation of the end effector 806 between a first position and a second position. As depicted in FIG. 8, the first and second movable portions 816, 818 are jaws of a grasper, although other movable portions can be used.

In some cases, a movable portion of an end effector 806 can have a proximal end that sticks out beyond a circumference of the distal hub 812 when in the first or second position. As depicted in FIG. 8, the first and second movable portions 816, 818 of surgical tip 802 have proximal ends 838 that move along a path during actuation of the end effector 806, which path takes the proximal ends 838 outside of the circumference of the distal hub 812. The distal hub 812 can include one or more slots through which the proximal ends 838 may pass. The proximal hub 814 can overlap a portion of the distal hub 812 up to or approximately up to such slot(s). In some cases, such as if no slot exists because the proximal ends of the end effector remain within the circumference of the distal hub during actuation, the proximal hub can overlap a portion of the distal hub that extends for up to or approximately up to the pivot 820 or up to or approximately up to the distal end of the distal hub.

The multi-part hub 808 can comprise a distal hub 812 coupled to a proximal hub 814. While the distal hub 812 can be made of a metal, such as the same metal used for the end effector 806 and/or the yoke 810, the proximal hub 814 can be made of an insulator, such as PEEK. The proximal hub 814 can overlap and surround a portion of the distal hub 812, although that need not always be the case.

The surgical tip 800 can removably couple to a control shaft 804. The control shaft 804 can include an inner shaft 828 and an outer shaft 826. For illustrative purposes, the outer shaft 826 is depicted in a partial-cutaway view and the inner shaft 828 is shown in a cutaway side view.

The inner shaft 828 can be axially movable within the outer shaft 826 to facilitate actuation of the end effector 806 via axially moving the yoke 810. The inner shaft 828, as well as the yoke 810 and end effector 806, can be made of electrically conductive materials, such as electrically conductive metal. The outer shaft 826 can be made of an electrically insulating material, such as PEEK. The outer shaft 826 can be made of the same material as the proximal hub 814.

The proximal hub 814 can removably couple to the outer shaft 826 of the control shaft 804 and the yoke 810 can removably couple to the inner shaft 828 of the control shaft 804. The proximal hub 814 can include threads 822 (e.g., internal threads) that engage threads 830 (e.g., external threads) of the outer shaft 826. The yoke 810 can include threads 824 (e.g., external threads) that engage threads 832 (e.g., internal threads) of the inner shaft 828. For illustrative purposes, threads 822 are depicted in dotted line for surgical tip 800. In some cases, threads 822, 824 are coaxial. Likewise, threads 830, 832 can be coaxial.

As used herein with regards to FIG. 8 and other suitable figures, movement of an inner shaft 828 or movement of a yoke 810 refers to movement of the inner shaft 828 or yoke 810 with respect to the outer shaft 826 or hub 808, respectively. Because the hub 808 is axially fixed with respect to the outer shaft 826 via a coupling (e.g., threaded coupling) between the outer shaft 826 and the proximal hub 814, and because the inner shaft 828 is axially fixed to the yoke 810 via a coupling (e.g., threaded coupling), movement of the inner shaft 828 axially with respect to the outer shaft 826 causes the yoke 810 to move axially with respect to hub 808, thus actuating the end effector to move between first and second positions.

Proximal hub 814 can have a flared profile wherein the outer diameter of the proximal hub 814 changes across its length. In some cases, the proximal end of the proximal hub 814 can have a diameter that matches a diameter of an outer shaft of a control shaft. In some cases, the outer diameter of the proximal hub 814 can increase moving distally from the proximal end of the proximal hub 814. In some cases, the outer diameter of the proximal hub 814 can increase moving distally from the proximal end of the proximal hub 814 to a maximum diameter, then decrease moving distally towards the distal end of the proximal hub 814. The profile of the proximal hub 814 can have any suitable contour (e.g., convex or concave) or combination of contours. In some cases, the maximum outer diameter of the proximal hub 814 can have a radial extent from a centerline of the hub 808 that is equal to or approximately equal to a maximum radial extent of the proximal end 838 of the end effector 806. For example, as depicted with reference to surgical tip 802 of FIG. 8, the proximal end 838 can extend radially from a centerline of the hub 808 by the same amount or approximately the same amount as the maximum outer diameter of the proximal hub 814.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is a surgical tip comprising: an end effector movable from a first position to a second position, the end effector having a distal region for contacting tissue and a proximal region; a yoke coupled to the proximal region of the end effector for manipulating the end effector between the first position and the second position, wherein the yoke comprises a threaded proximal end, wherein the yoke and the end effector are made of an electrically conductive material, and wherein the yoke and the end effector are electrically coupled; and a hub positioned around the yoke, wherein the hub comprises a distal hub and a proximal hub, wherein the end effector is coupled to the distal hub at a pivot, wherein the proximal hub is made of a non-conductive material, and wherein the proximal hub comprises a proximal threaded end.

Example 2 is the surgical tip of example(s) 1, wherein the proximal hub is made of Polyetheretherketone.

Example 3 is the surgical tip of example(s) 1 or 2, wherein the proximal hub is coupled to the distal hub by a threaded connection.

Example 4 is the surgical tip of example(s) 1-3, wherein the proximal hub is coupled to the distal hub with an epoxy.

Example 5 is the surgical tip of example(s) 1-4, wherein the threaded proximal end of the yoke and the threaded proximal end of the proximal hub are coaxially threaded.

Example 6 is the surgical tip of example(s) 1-5, wherein the proximal hub surrounds a portion of the distal hub.

Example 7 is the surgical tip of example(s) 1-6, wherein the end effector is selected from the group consisting of scissors, graspers, a punch, and dissectors.

Example 8 is the surgical tip of example(s) 1-7, wherein the distal hub includes a slot for receiving the proximal region of the end effector during movement of the end effector between the first position and the second position, and wherein the proximal hub surrounds a portion of the distal hub located proximally beyond the slot.

Example 9 is the surgical tip of example(s) 1-8, wherein the proximal hub is made of material having a dielectric strength of at or greater than 130 KV/cm.

Example 10 is the surgical tip of example(s) 1-9, wherein the proximal hub has an outer diameter of at or less than 6.0 mm.

Example 11 is the surgical tip of example(s) 1-10, wherein the proximal hub is made of an autoclavable and sterilizable material.

Example 12 is the surgical tip of example(s) 1-11, wherein the proximal hub is made of a material having a glass transition temperature at or above 120° C.

Example 13 is the surgical tip of example(s) 1-12, wherein a length between a distal end of the distal hub and a proximal end of the yoke is at or less than 5 cm.

Example 14 is the surgical tip of example(s) 1-13, wherein a length between a distal end of the end effector and a proximal end of the yoke is at or less than 9 cm.

Example 15 is the surgical tip of example(s) 1-14, wherein the end effector comprises a stationary portion and a movable portion, wherein the stationary portion is fixed with respect to the hub.

Example 16 is the surgical tip of example(s) 1-15, wherein the end effector comprises a first movable portion and a second movable portion, wherein the first movable portion and the second movable portion move with respect to the hub during movement of the end effector between the first position and the second position.

Example 17 is a surgical apparatus comprising: the surgical tip of example(s) 1-16; and a handpiece couplable to the surgical tip, wherein the handpiece comprises an inner shaft movable axially within an outer shaft, wherein the outer shaft is couplable to the proximal hub by the proximal threaded end of the proximal hub, and wherein the inner shaft is couplable to the yoke by the threaded proximal end of the yoke.

Example 18 is the surgical apparatus of example(s) 17, wherein the outer shaft is made of the same material as the proximal hub.

Example 19 is the surgical apparatus of example(s) 17 or 18, wherein the outer shaft has an outer diameter that is the same size as an outer diameter of the proximal hub.

Example 20 is the surgical apparatus of example(s) 17-19, wherein the handpiece further comprises a cautery pin electrically coupled to the inner shaft to convey electrical signals through the inner shaft and the yoke to the end effector when the surgical tip is coupled to the handpiece.

Example 21 is the surgical apparatus of example(s) 17-20, further comprising an additional surgical tip, wherein the handpiece is couplable to the additional surgical tip after decoupling of the surgical tip from the handpiece, wherein the additional surgical tip comprises an additional end effector that is different from the end effector of the surgical tip.

Example 22 is a method, comprising: providing the surgical tip of example(s) 1-16; coupling the surgical tip to a handpiece, wherein the handpiece comprises an inner shaft movable axially within an outer shaft, and wherein coupling the surgical tip to the handpiece comprises coupling the outer shaft of the handpiece to the proximal hub of the surgical tip by the proximal threaded end of the proximal hub, and coupling the inner shaft of the handpiece to the yoke of the surgical tip by the threaded proximal end of the yoke; decoupling the surgical tip from the handpiece; and autoclaving the surgical tip.

Example 23 is the method of example(s) 22, further comprising: coupling the autoclaved surgical tip to the handpiece or an additional handpiece; and contacting tissue with the end effector of the surgical tip during a surgical procedure.

Example 24 is the method of example(s) 22 or 23, further comprising applying electrical current to tissue through the yoke and the end effector.

Example 25 is the method of example(s) 24, wherein the electrical current conveyed through the yoke is not conveyed through the proximal hub.

What is claimed is:

1. A surgical tip comprising:
    an end effector comprising at least one movable portion movable from a first position to a second position, the end effector having a distal region for contacting tissue and a proximal region;
    a yoke coupled to the proximal region of the end effector for manipulating the at least one movable portion between the first position and the second position, wherein the yoke comprises a threaded proximal end, wherein the yoke and the end effector are made of an electrically conductive material;

a hub positioned around the yoke, wherein the hub comprises:

a distal hub made of a conductive material, wherein a proximal portion of the at least one movable portion extends outside of a circumference of the distal hub in the first position or the second position; and a proximal hub externally surrounding a portion of the distal hub, wherein the proximal hub is made of a non-conductive material, and wherein the proximal hub comprises a proximal threaded end and a distal end; and a pivot passing through the distal hub, the pivot coupling the end effector to the distal hub.

2. The surgical tip of claim 1, wherein the at least one movable portion comprises:

a pivot hole aligned coaxially with the pivot of the distal hub; and a slot configured to receive a pin of the yoke.

3. The surgical tip of claim 2, wherein the proximal hub surrounds a portion of the distal hub located proximally beyond the slot.

4. The surgical tip of claim 1, wherein at least a portion of the end effector is rotatable around the pivot to move between the first position and the second position.

5. The surgical tip of claim 1, wherein the proximal hub includes a first diameter at the proximal threaded end and a second diameter at the distal end, wherein the first diameter is smaller than the second diameter.

6. The surgical tip of claim 1, wherein the proximal hub is coupled to the distal hub by a threaded connection.

7. The surgical tip of claim 6, wherein the proximal hub is further coupled to the distal hub with an epoxy.

8. The surgical tip of claim 1, wherein the threaded proximal end of the yoke and the threaded proximal end of the proximal hub are coaxially threaded.

9. The surgical tip of claim 1, wherein the end effector is selected from the group consisting of scissors, graspers, a punch, and dissectors.

10. The surgical tip of claim 1, wherein the proximal hub is made of an autoclavable and sterilizable material.

11. The surgical tip of claim 1, wherein the end effector further comprises a stationary portion fixed with respect to the hub.

12. The surgical tip of claim 1, wherein the end effector comprises a first movable portion and a second movable portion, wherein the first movable portion and the second movable portion move with respect to the hub during movement of the end effector between the first position and the second position.

13. A surgical apparatus comprising:

the surgical tip of claim 1; and a handpiece couplable to the surgical tip, wherein the handpiece comprises an inner shaft movable axially within an outer shaft, wherein the outer shaft is couplable to the proximal hub by the proximal threaded end of the proximal hub, and wherein the inner shaft is couplable to the yoke by the threaded proximal end of the yoke.

14. The surgical apparatus of claim 13, wherein the outer shaft has an outer diameter that is the same size as an outer diameter of the proximal hub.

15. The surgical apparatus of claim 13, wherein the handpiece further comprises a cautery pin electrically coupled to the inner shaft to convey electrical signals through the inner shaft and the yoke to the end effector when the surgical tip is coupled to the handpiece.

16. The surgical apparatus of claim 13, further comprising an additional surgical tip, wherein the handpiece is couplable to the additional surgical tip after decoupling of the surgical tip from the handpiece, wherein the additional surgical tip comprises an additional end effector that is different from the end effector of the surgical tip.

17. A method, comprising:

providing the surgical tip of claim 1;

coupling the surgical tip to a handpiece, wherein the handpiece comprises an inner shaft movable axially within an outer shaft, and wherein coupling the surgical tip to the handpiece comprises coupling the outer shaft of the handpiece to the proximal hub of the surgical tip by the proximal threaded end of the proximal hub, and coupling the inner shaft of the handpiece to the yoke of the surgical tip by the threaded proximal end of the yoke;

decoupling the surgical tip from the handpiece; and autoclaving the surgical tip.

18. The method of claim 17, further comprising:

coupling the autoclaved surgical tip to the handpiece or an additional handpiece; and contacting tissue with the end effector of the surgical tip during a surgical procedure.

19. The method of claim 17, further comprising applying electrical current to tissue through the yoke and the end effector.

20. The method of claim 19, wherein the electrical current conveyed through the yoke is not conveyed through the proximal hub.

* * * * *